United States Patent [19]

Diedrichsen et al.

[11] Patent Number: 4,462,980

[45] Date of Patent: Jul. 31, 1984

[54] STABILIZED PLASMIN COMPOSITIONS AND METHOD FOR PREPARATION THEREOF

[75] Inventors: Allan Diedrichsen, Rødovre; Marie Johannessen, Birkerød; Peter Tang, Tåstrup, all of Denmark

[73] Assignee: Novo Industri A/S, Denmark

[21] Appl. No.: 336,788

[22] Filed: Jan. 4, 1982

[30] Foreign Application Priority Data

Jan. 5, 1981 [GB] United Kingdom ............... 8100133

[51] Int. Cl.³ .................... A61K 43/00; A61K 49/02
[52] U.S. Cl. ........................... 424/1.1; 424/9; 424/177; 260/112 R
[58] Field of Search ............ 424/1, 94, 9, 177, 1.1, 424/1.5; 436/8, 69, 86; 252/301.1; 260/429.1, 112 R

[56] References Cited

U.S. PATENT DOCUMENTS

| | | | |
|---|---|---|---|
| 3,720,761 | 3/1973 | Hunter, Jr. | 424/1 |
| 3,863,004 | 1/1975 | Wolfangel | 424/1 |
| 3,950,513 | 4/1976 | Jensen | 424/94 |
| 4,048,296 | 9/1977 | Wolfangel | 424/1 |
| 4,062,933 | 12/1977 | Wolfangel | 424/1 |
| 4,297,344 | 10/1981 | Schwinn et al. | 424/101 |

*Primary Examiner*—Benjamin R. Padgett
*Assistant Examiner*—M. Moskowitz
*Attorney, Agent, or Firm*—Fidelman, Wolffe & Waldron

[57] ABSTRACT

Novel plasmin compositions, conditioned for labelling with technetium-99m by containing a pertechnetate reducing reagent, and plasmin admixed with a plasmin stabilizing agent.

The novel compositions are particularly suited for the preparation of technetium-99m labelled plasmin used as a scintigraphic scanning agent for the detection of venous thrombosis.

12 Claims, No Drawings

STABILIZED PLASMIN COMPOSITIONS AND METHOD FOR PREPARATION THEREOF

This invention relates to compositions which are useful in the preparation of a scintigraphic scanning agent in which the the radionucleide is technetium-99m, and to a process for preparing such compositions.

More specifically, the present invention is directed to novel compositions comprising stabilized plasmin as a prospective carrier for technetium-99m, and to a process for preparing such plasmin compositions. Technetium-99m labelled plasmin has proved particularly useful as a scintigraphic scanning agent for the detection of deep vein thrombosis (DVT) located in the patient's limbs, particularly in the legs.

BACKGROUND OF THE INVENTION

DVT, whether accompanied by pulmonary embolism or not, is a potentially serious complication of many surgical and medical conditions which requires early diagnosis as a basis for prompt and appropriate treatment in order to counteract serious sequelae. The incidence of DVT is appreciable under traumatic conditions, such as those associated with major surgery or bone fracture (particularly of the neck of femur). Furthermore, it is well recognized that any condition of enforced immobility, such as advanced age, obesity, neoplasm and cardiac failure or infarction enhances the risk of developing DVT.

The correct clinical diagnosis of DVT is impeded by the fact that clinical symptoms and signs thereof tend to be rather unspecific and often unreliable. Thus the clinical diagnosis of DVT based on such symptoms as venous distension, pain, tenderness and swelling of the affected limb with increased skin temperature has often proved to give false positive results. Contrarywise, it has also been recognized that even extensive DVT may occur in the absence of conspicuous physical signs if the main veins are not completely occluded and that, in fact, a substantial number of patients with DVT do not show clinical evidence thereof.

The inadequacy of clinical examination has led to the search for objective diagnostic tests for the detection of DVT. Over the years a variety of such tests, ranging from X-ray phlebography over methods based on monitoring blood flow (for example by Doppler ultrasound technique or impedence plethysmography) to localization of thrombi by means of radiopharmaceuticals, have become available to the medical profession. The latter group of tests makes use of radiopharmaceuticals having the ability to accumulate in fibrinous clots, thereby enabling their dectection, for example by scintigraphic scanning procedures. Exemplary of such radiopharmaceuticals are radioiodinated fibrinogen and technetium-99m labelled plasmin. Whereas the labelled fibrinogen is incorporated rather slowly into the developing thrombus, extraneous labelled plasmin has been found to accumulate rapidly even in established fibrinous clots.

Mammalian blood contains an enzymatic system which is called the fibrinolytic enzyme system. Under normal conditions a dynamic equilibrium is maintained where fibrin deposits are dissolved by local activation of the fibrinolytic enzyme system. Endogenous activators, for example the so called plasminogen tissue activator, convert the circulating plasminogen into the fibrinolytically active enzyme plasmin which has a high affinity for fibrin. Among exogenous activators of the fibrinolytic enzyme system mention may be made of streptokinase which is generated by certain strains of haemolytic streptococci, urokinase which is recoverable from human urine or produced in tissue culture, and trypsin.

Owing to its fibrinolytic effect infusion of exogenous plasmin has been used as an alternative to other methods in thrombolytic therapy. To satisfy the requirements for such therapeutic purposes plasmin may be prepared from purified plasminogen by activation with streptokinase or, more frequently, with urokinase or trypsin.

For diagnostic purposes the detection of fibrin containing thrombi may be achieved by injection of small amounts of radiolabelled plasmin. Due to the rapidly established association of radiolabelled plasmin with fibrinous clots, particularly in comparison with such agents as radioiodinated fibrinogen, the technetium-99m plasmin test has been shown to be a highly sensitive and versatile procedure which is well adapted for relatively fast routine screening of patients for developing as well as established DVT (vide British Journal of Radiology, vol. 53 (1980) p. 673, J. M. Deacon et al.).

The same reference describes a technetium-99m plasmin kit in which the plasmin is admixed with sodium chloride together with stannous chloride as the $^{99}Tc^m$-pertechnetate reducing agent. This method for labelling plasmin with technetium-99m was first described by R. B. R. Persson and L. Darte (Int. Journal of Applied Radiation and Isotopes, vol. 28 (1977) p. 97).

The technetium-99m plasmin kit, comprising a lyophilized mixture of plasmin and stannous chloride, has been available for some time to hospitals engaged in trial programmes directed to the evaluation of the technetium-99m-plasmin test as a screening method for diagnosing DVT. The kit has been supplied by NOVO INDUSTRI A/S, Copenhagen under the name "LYSOFIBRIN kit for $^{99}Tc^m$-labelling" (LYSOFIBRIN is registered trade mark for highly purified porcine plasmin).

It has been found, however, that the plasmin incorporated into this kit is not sufficiently stable for its intended use unless the kit is permanently stored at a temperature not exceeding $-20°$ C. Thus at the ordinary refrigerator temperature of $5°$ C. inactivation of plasmin proceeds at a rate of approximately 5 per cent per month. Since retention of proteolytic activity of plasmin is believed to be a prerequisite for its affinity to fibrin, which property confers specificity on the radiolabelled plasmin for thrombi, the instability problem should be eliminated before the kit is made available for general clinical use.

It is an object of the present invention to devise plasmin compositions conditioned for technetium-99m labelling which are devoid of the shortcomings pertaining to the composition described hereinbefore.

It is a further object of this invention to provide a process for preparing such plasmin compositions in which the plasmin is stabilized to the extent that the composition is suited for its intended use even after storage for extended periods of time under ambient conditions.

The attainment of these objects are based on the discovery that certain polyhydroxy compounds, when incorporated into the composition, elicit a pronounced stabilizing effect on the plasmin therein without, however, interfering substantially neither with the yield of technetium-99m plasmin obtained in a subsequent labelling process conducted under standardized conditions nor with the radiochemical purity of the resulting radiopharmaceutical.

Glycerol is used as a stabilizer of plasmin in aqueous solution, usually at a concentration of about 50 percent of the solution, i.e. vastly in excess of plasmin on a weight basis. However, liquid polyhydroxy compounds are not contemplated for the compositions of this invention due to the mandatory presence therein of a strongly reducing agent which may be susceptible to liquid phase deterioration. Hence, the stabilized plasmin compositions of this invention are in solid form. Furthermore, it may be mentioned that the stabilizers usable for labelling purposes should generally be physiologically acceptable, should not themselves be labelled under labelling conditions preferred herein, and should not interfere with the labelling of plasmin.

Polyhydroxy compounds, such as sugars and sugar alcohols, are known as stabilizers of proteolytic enzymes, particularly in liquid formulations thereof, in which inactivation is believed to be caused mainly by enzyme autodigestion. However, the problem facing the inventors in the present case is a different one, firstly because the plasmin compositions of the present invention are solid, and secondly because they are prepared and used under acid conditions where the plasmin therein is proteolytically inactive. Therefore, inactivation must be caused by other factors than autodigestion.

As will be outlined subsequently, it has surprisingly been found that the polyhydroxy compounds devised herein prevent or at least impede the aggregation of plasmin. Since such plasmin aggregates are believed to represent initial stages of denatured plasmin, their presence in the compositions of this invention is undesirable.

SUMMARY OF THE INVENTION

According to its first aspect the present invention provides a solid form plasmin composition adapted for labelling with technetium-99m by being admixed with a pertechnetate reducing agent, which composition comprises an effective amount of a plasmin stabilizing polyhydroxy compound selected from the group consisting of the pentitols xylitol and ribitol; meso-inositol; the monosaccharides glucose, mannose, galactose, fructose, and sorbose; and the disaccharides sucrose and maltose.

According to its second aspect the present invention provides a method of preparing a solid form plasmin composition adapted for labelling with technetium-99m by being admixed with a pertechnetate reducing agent, which method comprises admixing in solution plasmin and an effective amount of a plasmin stabilizing polyhydroxy compound selected from the group consisting of the pentitols xylitol and ribitol; meso-inositol; the monosaccharides glucose, mannose, galactose, fructose, and sorbose; and the disaccharides sucrose and maltose, followed by lyophilizing the mixture to solid form.

According to a further aspect there is provided a scintigraphic scanning agent for diagnostic purposes, which agent comprises the composition of the present invention labelled with technetium-99m.

According to still another aspect there is also provided the use as scintigraphic scanning agent of a composition according to the present invention, labelled with technetium-99m.

It is to be understood that throughout this specification and the claims thereof the term "plasmin" encompasses also compounds which, whilst retaining their biological properties, are derived from plasmin by fragmentation. Exemplary of such compounds is "miniplasmin", which is fibrinolytically active, vide U. Christensen et al. (Biochim.Biophys.Acta 567 (1979), pp. 472–481), incorporated herein by reference.

DETAILED DESCRIPTION OF THE INVENTION

The source of plasmin used in practicing this invention is not essential. It may be recovered from blood plasma obtained from a variety of mammalian species, including man. However, highly purified plasmin of porcine origin is preferred. A purified grade of plasminogen may be obtained by the method described by D. G. Deutsch and E. T. Metz (Science, vol. 170 (1970), pp. 1095–1096). The conversion of plasminogen into plasmin by the action of urokinase may be conducted according to the method of B. Wiman and P. Wallén (Europ.J.Biochemistry, vol 36 (1973), pp. 25–31), and with trypsin as described by K. Jacobsen (Acta.-Chem.Scand., vol. 7 (1953), pp. 430–434). A preferred preparation of plasmin is made by lyophilization of an acidic aqueous plasmin solution having an activity of at least 3 NOVO units (NU) per mg. The unit activity of plasmin is defined as the activity which under specified conditions (i.e. 35° C. and pH 7.5) in the course of 20 minutes gives rise to the formation from a standard casein preparation, of perchloric acid soluble peptides equivalent to an increase in absorbance at 275 nm of 1. For further reference, vide: Pharmaceutical Enzymes (Eds.: R. Ruyssen and A. Lauwers) E. Story-Scientia 1978, p. 123 ff.

A number of pertechnetate reducing agents, organic as well as inorganic, are known in the art. In this connection mention may by made of stannous, ferrous and chromous salts of inorganic acids, in particular hydrochloric and sulfuric acid, and ascorbic acid. In a preferred embodiment of the present invention the pertechentate reducing agent is a stannous salt, preferably stannous chloride.

The amount of pertechnetate reducing agent incorporated into the compositions of this invention should be adjusted so as to ascertain under otherwise optimum labelling conditions, such as those specified subsequently, the highest possible labelling efficiency of the radionucleide (in casu technetium-99m in its lower than +7 valence states). The reducing agent should be present in an amount effective for such purpose. On the other hand, owing to their general toxicity the incorporation of excessive amounts of such agents as stannous or chromous salts should be avoided.

The amount of stannous chloride incorporated according to a preferred mode of this invention should be chosen in the range of from 0.8–16, perferably from 2 to 8, percent by weight of plasmin, the amount of plasmin hereinafter being calculated on the basis of a product with an activity of 3.5 NU per mg.

The weight ratio of polyhydroxy compound to plasmin contemplated for the compositions of this invention should normally be in the range of from 0.1:1 to 10:1, preferably from 0.5:1 to 5:1, the extreme limits being dictated by the attainment of a plasmin stabilizing effect which is satisfactory for all practical purposes, such as conditions to which the product is likely to be exposed during distribution and storage. It may be mentioned in passing that none of the polyhydroxy compounds selected for the practice of this invention were found to have any adverse effects on the enzymatic activity of plasmin in amounts up to 10 times that of plasmin.

However, incorporation of a polyhydroxy compound in amounts exceeding 10 times that of plasmin is not recommendable, because for such compositions the point of maximum stability is generally surpassed.

The compositions of this invention may be prepared by dissolving the plasmin together with the pertechnetate reducing agent and the plasmin stabilizing polyhydroxy compound in distilled water which is constantly chilled and kept deoxygenated by means of a nitrogen stream. In the preferred mode where the pertechnetate reducing agent is a stannous salt, pH of the solution is adjusted to 3, whereafter aliquots, each containing for example 35 NU (corresponding to about 10 mg) of plasmin, are transferred to sterile vials, quickly frozen and lyophilized.

With stannous chloride as the pertechnetate reducing agent labelling is generally conducted at pH 2.0–2.2, usually with 0.5 mCi (18.5 MBq) of pertechnetate per unit activity of plasmin, the pertechnetate being eluted from a commercial generator by means of an isotonic sodium chloride solution. Further details of a currently used labelling procedure have been published in the literature, for example by J. M. Deacon et al. (vide supra) and by L. Darte and R. B. R. Persson (Journal of Liquid Chromatography vol. 2 (1979) p. 499).

Labelling results

The method described in the latter reference for controlling the quality (primarily in terms of labelling yield and radiochemical purity) of technetium-99m labelled plasmin preparations is also applicable to testing the labelling performance of the plasmin compositions of the present invention. The gel chromatography scanning method, in which the labelled preparation is subjected to chromatography on a Sephadex G-25 column whereafter the radioactive constituents distributed along the column are detected by scintigraphic scanning and their relative amounts subsequently determined from the recorded scanning profile, has proved particularly useful for that purpose.

Application of this test procedure (and a variant thereof in which gel chromatography is substituted with thin layer chromatography, cf. Darte and Persson, supra) to plasmin preparations labelled in the presence of a variety of polyhydroxy compounds or for conducting control experiments on such polyhydroxy compounds in the absence of plasmin gave results as shown in Table I below.

TABLE I

|  | $^{99}Tc^m$-labelling of stabilizing agent | $^{99}Tc^m$-labelling of plasmin/plasminogen in the presence of 2.5 parts of stabilizing agent | |
|---|---|---|---|
|  |  | labelling yield (%) | Interference from stabilizing agent |
| Pentitols |  |  |  |
| Xylitol | none | 81 | not detectable |
| Ribitol | " | 79 |  |
| Hexitols |  |  |  |
| Sorbitol | none | 56 | appreciable |
| Mannitol | " | 70 |  |
| Hexoses |  |  |  |
| Glucose | none | 78 | not detectable |
| Mannose | " | 80 |  |
| Galactose | " | 80 |  |
| Fructose | " | 82 |  |
| Sorbose | " | 79 |  |
| Hexose Disaccharides |  |  |  |

TABLE I-continued

|  | $^{99}Tc^m$-labelling of stabilizing agent | $^{99}Tc^m$-labelling of plasmin/plasminogen in the presence of 2.5 parts of stabilizing agent | |
|---|---|---|---|
|  |  | labelling yield (%) | Interference from stabilizing agent |
| Sucrose | none | 87 | not detectable |
| Maltose | " | 82 |  |
| Lactose | appreciable | — |  |
| Inositols |  |  |  |
| Meso-inositol | none | 85 | not detectable |

Considering that an 80 percent yield has been reported by labelling glucose with technetium-99m at pH 4 (British patent application No. 2,016,198) it is surprising that no labelling of the polyhydroxy compounds of the present invention was observed under the labelling conditions preferred herein, i.e. pH 2.0–2.2.

Aggregation of native plasmin

The formation of plasmin aggregates was investigated by subjecting plasmin compositions (labelled or unlabelled) to DISC electrophoresis on polyacrylamide (7.5%) in a pH 4.5 buffer containing 3M urea following the procedure of R. Mauerer (Disk Electrophorese, Walter de Gruyter, Berlin 1968).

The fact that identical electrophoretic patterns were obtained for unlabelled and labelled plasmin preparations, developed by staining and scintigraphic scanning, respectively, demonstrates that labelling in itself does not induce transformations of native plasmin. However, quantitative scanning of electropherograms obtained from the old (sodium chloride containing) composition after labelling revealed that extensive transformation of plasmin had taken place. Another sample (20 µl) was subjected to High Pressure Liquid Chromatography on a Waters protein analyses column I-125 (Waters Associates, Inc. Mass., USA), the elution being conducted with phosphoric acid (0.2M) at a flow rate of 0.25 ml/min.(maximum pressure 200 p.s.i.) and monitored at 276 nm. The chromatogram indicated that extensive transformation of plasmin to high molecular weight compounds or aggregates had occurred. Furthermore, counting of the collected fractions (each of 125 µl) demonstrated extensive labelling of aggregated plasmin.

Application of the same analyses to the plasmin compositions of the present invention invariably demonstrated a substantial suppression of aggregate formation and, furthermore, that this inhibitory effect was optimal at stabilizer concentrations within the preferred ranges of this invention. The analytical data showed also that labelling of the compositions according to this invention took place predominantly on native plasmin, thus affording labelled compositions of substantially higher radiochemical purity than those known in the art.

The highest radiochemical purity was obtained with mono- and disaccharides. Accordingly, in a preferred embodiment of the present invention the stabilizing polyhydroxy compound is a mono- or disaccharide. Still more preferred is a polyhydroxy compound selected from the group consisting of fructose, sucrose, and maltose.

The significance of these findings is underlined by the results of other experiments from which it may be inferred that native plasmin has a significantly higher affinity for fibrin than aggregated plasmin. In addition, there are certain indications to the effect that aggregated plasmin differs from native plasmin with respect to its biodistribution, in that the former accumulates predominantly in the liver whereas the latter is more evenly distributed between liver and kidney. Therefore, the formation of plasmin aggregates is undesirable also from a dosimetric point of view.

The present invention is illustrated in further detail by way of the following examples which, however, are not to be construed as limiting the scope thereof.

EXAMPLE 1

A plasmin composition with a weight ratio of stabilizing polyhydroxy compound to plasmin of 2.5 was prepared in the following manner:

Distilled water (500 ml) acidified with N hydrochloric acid (100 μl) was deoxygenated by boiling for 30 minutes and then chilled in ice-water while being kept oxygen-free by means of a stream of nitrogen. pH was adjusted to 3.0 with N hydrochloric acid.

Plasmin (2.50 g, lyophilized plasmin (or fibrinolysin) having an activity of at least 3 NOVO units per mg is supplied by Sigma Chemical Co., MO, U.S.A.), stabilizing agent (6.25 g) and stannous chloride dihydrate (113 mg) were weighed out, whereafter dissolution in the above prepared, deoxygenated water (250 ml) was effected while nitrogen was constantly passed through the solution. Following adjustment of pH to 3.0 (with hydrochloric acid or sodium hydroxide), 1.0 ml aliquots of the solution were transferred to 5 ml vials which were then provided with freeze drying stoppers. The contents were quickly frozen in dry ice and then lyophilized. The vials were closed in a nitrogen atmosphere and then immediately provided with capsules.

Accelerated stability tests were conducted by storing the compositions so prepared at 35° C. for one month, whereafter the residual plasmin activity was measured relative to that of the same preparations stored at −20° C. For comparison, the same test was conducted with the prior art composition, in which the polyhydroxy compound was substituted with sodium chloride (14.5 mg). The results are presented in the following Table II.

TABLE II

| Stabilizing agent | Average residual activity (%) |
|---|---|
| Pentitols | |
| Xylitol | 73 |
| Ribitol | 75 |
| Hexoses | |
| Glucose | 95 |
| Mannose | 93 |
| Galactose | 88 |
| Fructose | 93 |
| Sorbose | 96 |
| Hexose Disaccharides | |
| Sucrose | 99 |
| Maltose | 100 |
| Inositols | |
| Meso-inositol | 95 |
| Prior art composition (sodium chloride) | 35 |

EXAMPLE 2

Plasmin compositions in which the plasmin and stannous chloride contents were kept constant while the weight ratio of stabilizer to plasmin was varied were prepared by a procedure analogous to that described in Example 1.

Such compositions were prepared with fructose, sucrose, and meso-inositol as stabilizing agents, and subjected to the accelerated stability test described in Example 1. The results are shown in the following table III:

TABLE III

| Stabilizing agent | Weight ratio of stabilizing agent to plasmin | Average residual activity (%) after 1 month at 35° C. |
|---|---|---|
| Sucrose | 0.5 | 99 |
| | 1.5 | 103 |
| | 2.5 | 103 |
| | 5 | 99 |
| | 10 | 102 |
| Fructose | 0.5 | 95 |
| | 2.5 | 93 |
| | 5 | 75 |
| Meso-inositol | 0.5 | 96 |
| | 2.5 | 95 |
| | 10 | 92 |
| Prior art composition (NaCl, 14.5 mg) | — | 35 |

EXAMPLE 3

Miniplasminogen was prepared from porcine plasminogen according to the method described by L. Sottrup-Jensen et al. (Progress in Chemical Fibrinolysis and Thrombolysis, Vol. 3 (Ed.s: J. F. Davidson et al.) Raven Press, New York 1978, p. 200 ff.), the only modification being that the porcine plasminogen solution was diluted 2.5 times with ammonium carbonate buffer prior to digestion with elastase while the concentration of the latter and of pancreatic trypsin inhibitor were maintained at the values prescribed in the reference.

The conversion of miniplasminogen into miniplasmin was carried out as described by U. Christensen et al. (Biochim. Biophys.Acta, vide supra), whereby a preparation having a plasmin activity of 6.2 NOVO units (NU) per mg was obtained.

Two series of miniplasmin preparations, one with sucrose and one with sodium chloride, the latter corresponding to the known plasmin composition, were prepared in a similar manner as described in Example 1. Each vial contained 6.2 mg of miniplasmin, corresponding to 11 mg of plasmin (3.5 NU/mg). The other constituents were:

| Preparation | 1 (sucrose) | 2 (NaCl) |
|---|---|---|
| Stannous chloride (mg) | 0.45 | 0.45 |
| Stabilizer (mg) | 25 | — |
| Sodium chloride (mg) | — | 14.5 |
| pH (prior to lyophilization) | 3.0 | 2.0 |

Stability tests were conducted as illustrated in connection with Example 1. Technetium-99m labelling was performed according to the method described in the following Example 4 and the labelling performance of the miniplasmin preparations was evaluated by scintigraphic scanning as described previously. The following results were obtained:

| Preparation | Average residual activity (%) after 1 month at 35° C. | Labelling yield (%) |
|---|---|---|
| 1 (sucrose) | 98 | 72 |
| 2 (NaCl) | 92 | 65 |

EXAMPLE 4

The labelling procedure was the same irrespective of which stabilizing polyhodroxy compound was incorporated. To each vial was added, in the following order and under aseptic conditions, sterile solutions of:

Hydrochloric acid (0.30 ml of 0.1 N), $^{99}Tc^m$-pertechnetate (1.00 ml, corresponding to about 15 mCi (550 MBq)), eluted from a commercial pertechnetate generator (obtainable from The Radiochemical Centre, Ltd., Amersham, England) with 0.9 percent sodium chloride, and Sodium chloride (2.20 ml of 0.9 percent solution).

The vial was left to stand at room temperature for 1 hour to complete the labelling process.

The total activity of the contents of the vial was then counted. The dosage to be administered to each patient (usually 0.5 mCi or 18.5 MBq) can be calculated from the total activity by taking into account that the half-life of $^{99}Tc^m$ is 6 hours.

What we claim is:

1. A solid form plasmin composition adapted for labelling with technetium-99m by being admixed with a pertechnetate reducing agent, which composition comprises plasmin, a pertechnetate reducing agent and an effective amount of a plasmin stabilizing polyhydroxy compound selected from the group consisting of the pentitols xylitol and ribitol, meso-inositol, the monosaccharides glucose, mannose, galactose, fructose, and sorbose and the disaccharides sucrose and maltose.

2. The composition according to claim 1, wherein the plasmin is of porcine origin.

3. The composition according to claim 1, wherein the pertechnetate reducing agent stannous chloride in an effective amount forms part of the composition.

4. The composition according to claim 3, wherein the amount of stannous chloride is in the range of from 0.8 to 16 percent by weight of plasmin, the amount of plasmin being calculated on the basis of a product with an activity of 3.5 NOVO units per mg.

5. The composition according to claim 4, wherein the amount of stannous chloride is in the range of from 2 to 8 percent by weight.

6. A composition according to claim 1, wherein the weight ratio of polyhydroxy compound to plasmin is in the range of from 0.1:1 to 10:1.

7. The composition according to claim 6, wherein the weight ratio of polyhydroxy compound is in the range of from 0.5:1 to 5:1.

8. A composition according to claim 1, wherein the polyhydroxy compound is a mono- or disaccharide.

9. A composition according to claim 8, wherein the polyhydroxy compound is selected from the group consisting of fructose; sucrose, and maltose.

10. A method of preparing a solid form plasmin composition adapted for labelling with technetium-99m by being admixed with a pertechnetate reducing agent, which method comprises admixing in solution plasmin a pertechnetate reducing agent and an effective amount of a plasmin stabilizing polyhydroxy compound selected from the group consisting of the pentitols xylitol and ribitol meso-inositol the monosaccharides glucose, mannose, galactose, fructose and sorbose, and the disaccharides sucrose and maltose, followed by lyophilizing the mixture to solid form.

11. The method of claim 10 comprising admixing with the plasmin in solution an effective amount of stannous chloride.

12. A method for labelling plasmin wherein the solid form plasmin containing composition of claim 3 is dissolved and then reacted with pertechnetate in solution to form thereby the technetium-99m labelled plasmin.

* * * * *